United States Patent [19]

Stanley et al.

[11] 3,985,141
[45] Oct. 12, 1976

[54] INFLATION AND PRESSURE RELIEF VALVE

[75] Inventors: Theodore H. Stanley; Jerrold L. Foote, both of Salt Lake City, Utah

[73] Assignee: The University of Utah, Salt Lake City, Utah

[22] Filed: Mar. 10, 1975

[21] Appl. No.: 557,192

[52] U.S. Cl. .............................................. 128/351
[51] Int. Cl.² ...................................... A61M 16/00
[58] Field of Search .................................... 128/351

[56] References Cited
UNITED STATES PATENTS

| | | | |
|---|---|---|---|
| 3,683,931 | 8/1972 | Chelucci et al. | 128/351 |
| 3,731,691 | 5/1973 | Chen | 128/351 |
| 3,794,043 | 2/1974 | McGinnis | 128/351 |

OTHER PUBLICATIONS

Crosby, W.M., "Automatic Intermittent Inflation of Tracheostomy-Tube Cuff", IN The Lancet, No. 7358, vol. II for 1964, Sept. 5, 1964.

*Primary Examiner*—Channing L. Pace

[57] ABSTRACT

An inflation and adjustable pressure relief apparatus for the inflatable cuff of an endotracheal tube, the apparatus having an adjustably spring-biased relief valve to automatically release gas pressures from the cuff above a preselected pressure level and a manually operable spring-biased valve for increasing the gas pressure in the cuff.

3 Claims, 3 Drawing Figures

INFLATION AND PRESSURE RELIEF VALVE

BACKGROUND

1. Field of the Invention

This invention relates to inflation and automatic pressure relief valves for an inflatable cuff on an endotracheal tube.

2. The Prior Art

Endotracheal tubes are well-known in the medical arts and are used extensively for the ventilation of a patient's lungs particularly during periods of anesthesia. The endotracheal tube consists of a tube having an open end which is inserted into the patient's tracheal passage and is connected at the other end to an anesthetic gas delivery system. In order to function properly and provide suitable inflation of the lungs, it is necessary that the tracheal passage surrounding the endotracheal tube be sealed to prevent the escape of gases particularly during the inflation phase of the breathing cycle.

Historically, sealing of the tracheal passage has been accomplished by an inflatable cuff which is disposed as an annulus recessed from the tip of the endotracheal tube. The endotracheal tube includes a small cuff inflation lumen and an enlarged main lumen for the anesthesia gas delivery.

Early devices included a relatively unyielding inflatable cuff which, upon inflation, tended to require a relatively high pressure in order to adequately seal the tracheal passage against gas leakage. However, these relative high pressures exceeded the blood pressure within the surrounding tissue such that the tissue was deprived of an adequate blood supply resulting in ischemia and even necrosis of the underlying tissue. In some instances an over pressure would even result in stretching of the tracheal passage tissue.

Tissue damage and throat discomfort to the patient led to the development of lower pressure cuffs which were fabricated from a relatively pliant material and were designed to contact the internal surface of the tracheal passage over a greater surface area. Appropriate sealing of the tracheal passage could then be accomplished at a lower cuff inflation pressure.

The introduction of this latter improvement in endotracheal tubes has resulted in a further problem with respect to maintaining the appropriate cuff pressure. In particular, it has been discovered that the pliant cuff material acts as a semipermeable membrane toward the anesthetic gases. For example, anesthetic gases are generally constituted on the basis of about 60% nitrous oxide and 40% oxygen. Meanwhile, the cuff has been inflated with air (approximately 78% nitrogen and 20% oxygen). Since nitrous oxide is approximately 60% to 70% more difusable through a semi-permeable membrane when compared to nitrogen, a high proportion of nitrous oxide has been found to diffuse into the cuff and thereby increase the pressure.

It has been found that pressures as high as 350 millimeters of mercury have been recorded whereas the normal blood pressure is approximately 120 millimeters of mercury. Accordingly, the higher pressure in the cuff results in ischemia of the underlying tissue.

In view of the foregoing problem anesthesiologists have been known to inflate the cuff with the anesthetic gas, however, if the anesthetic gas is changed during the procedure, then the inflation gas within the cuff must also be changed.

It has also been known to incorporate an externally located balloon in gaseous communication with the cuff so as to receive excess gases absorbed into the cuff. The balloon is enclosed within a protective cover. Excessive quantities of gases received by the balloon cause the balloon to swell or expand to the limits imposed by the protective cover and thereby cause the pressure within the cuff to increase. This problem arises more frequently when restrictive areas in the trachea require a smaller diameter endotracheal tube and the cuff must, therefore, be inflated with a greater quantity of gas to compensate for the smaller diameter endotracheal tube.

In view of the foregoing, what is needed is an adjustable pressure relief valve which can be connected to the inflation lumen so as to relieve excess pressures that develop within the cuff. The relief valve should be adjustable to accomodate various pressure settings. Advantageously, the relief valve should include valve means for receiving the inflation gas for the cuff. The apparatus may also be inexpensively produced so as to be readily disposable. Such an invention is disclosed herein.

BRIEF SUMMARY AND OBJECTS OF THE INVENTION

The present invention is a valve which includes an adjustable spring-biased, relief valve and a manually operable infation valve within the same valve body. The pressure relief valve is adjustable between various pressure settings and also includes a device for holding the pressure relief valve in the closed position.

According to the method of this invention, the valve disclosed herein is connected to the inflation lumen of an endotracheal cuff and the pressure relief valve placed in the shut off position. The cuff is then inflated through the manually operable valve. A pressure setting is selected on the pressure relief valve to maintain the desired minimum pressure in the cuff to seal the tracheal passage. As pressures within the cuff build above the setting on the pressure relief valve during subsequent use, excess gas pressure in the cuff is automatically released from the cuff thereby maintaining a preselected pressure therein.

It is therefore an object of this invention to provide improvements in valves for an inflatable cuff of an endotracheal tube.

It is also an object of this invention to provide improvements in the method of maintaining a preselected pressure within an inflatable cuff of an endotracheal tube.

An even still further object of this invention is to provide an improved valve for an inflatable cuff of an endotracheal tube wherein a pressure relief valve and a manually operable inflation valve are included within the same valve body.

These and other objects and features of the present invention will become more fully apparent from the following description and appended claims taken in conjunction with the accompanying drawing.

DETAILED DESCRIPTION OF THE PREFERRED EMBODIMENTS

The invention is best understood by reference to the figures wherein like parts are designated with like numerals throughout.

Figure 1:
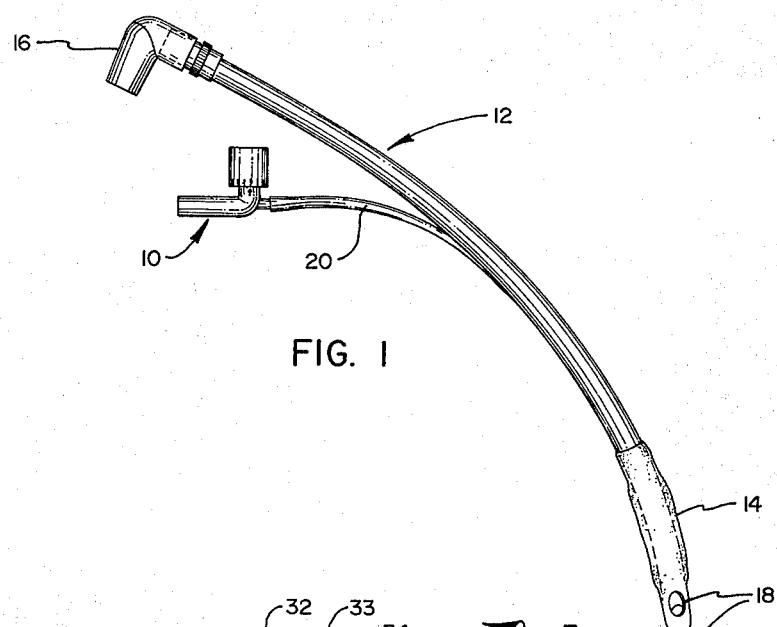
FIG. 1 is an elevational view of the valve apparatus of this invention in the environment of an endotracheal tube.

Referring now more particularly to FIG. 1, the valve of this invention is shown generally at 10 in combination with an endotracheal tube 12 which includes an inflatable cuff 14 at one end and an anesthesia gas delivery system fitting 16 at the other end. Fitting 16 serves to connect the endotracheal tube 12 to a conventional anesthesia gas delivery system (not shown) which in turn communicates the anesthetic gas/oxygen mixture to the patient through endotracheal tube 12 and ports 18 as is conventional. The diameter of endotracheal tube 12 is fixed by restrictions in the trachea.

Valve 10 is connected to an inflation lumen 20 for inflatable cuff 14. Valve 10 may be connected to the inflation lumen 20 by a number of conventional devices including, for example, a conventional fitting known as a Luer fitting. The primary consideration is that valve 10 is securely retained in inflation lumen 20 and is in gaseous communication with the interior of the inflatable cuff 14.

Figure 2:
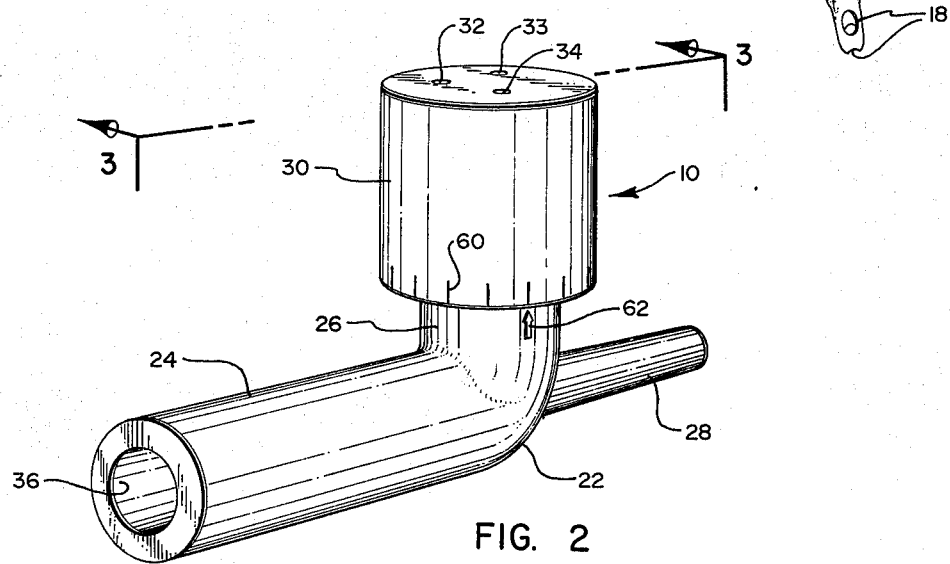
FIG. 2 is an enlarged perspective illustration of the valve apparatus of FIG. 1.

Referring now to FIG. 2, valve 10 includes a body 22 having an inflation valve 24, a pressure relief valve 26 and a hollow probe 28.

The pressure relief valve 26 is enclosed by a cap 30 having pressure relief ports 32–34 therein to permit the escape of gases as will be discussed more fully hereinafter with respect to FIG. 3. The periphery of cap 30 includes a plurality of indicia as indicated generally at 60 and are selectivly coordinated to indicate pressure settings at which pressure relief valve 26 will release pressure.

Figure 3:
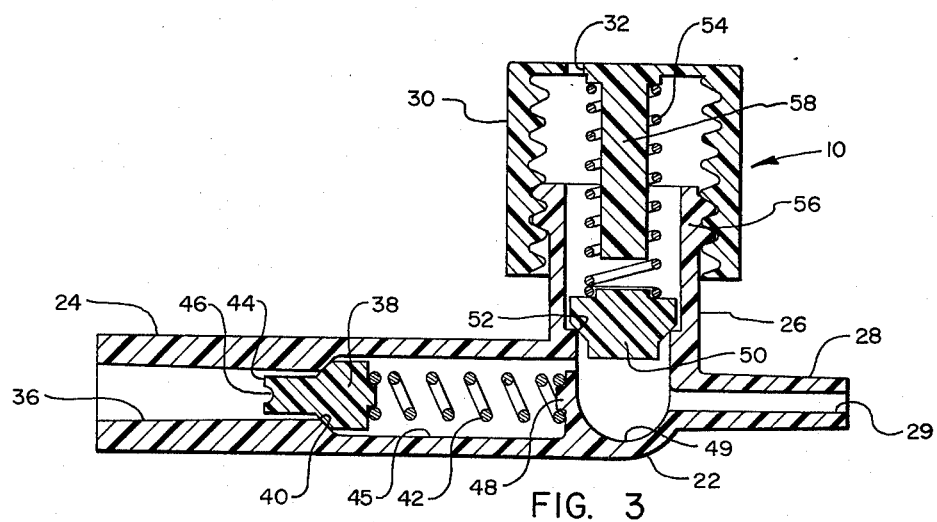
FIG. 3 is a cross section along lines 3—3 of FIG. 2.

Referring now more particularly to FIG. 3, the internal mechanism of valve 10 is more clearly shown. The flow path of valve 10 includes an inlet 36 which is obstructed by a manually operable stopper 38 of inflation valve 24.

Stopper 38 includes an axially located stem 44 which extends beyond valve seat 40 into inlet section 36 to thereby permit engagement and movement of stopper 38 away from valve seat 40 to allow the passage of gases from inlet 36 through chamber 45 into cavity 49 and from there through lumen 29 of probe 28 into inflatable cuff 14 (FIG. 1).

Stopper 38 is held against an inlet valve seat 40 by the action of a spring 42. Stem 44 includes a notch 46 in the end thereof to permit the escape of gases from an inflation device probe (not shown) which is inserted into inlet 36 and pressed against stem 44 to open inflation valve 24. Spring 42 cooperates against an upright flange 48 in valve body 22.

Relief valve 26 includes a valve body 50 which is held against a valve seat 52 by the compressive action of a spring 54. Spring 54 cooperates between valve body 50 and cap 30. Cap 30 is threadedly rotatable on a riser 56 to alter the pressure on spring 54. Cap 30 also has a boss 58 which can be used to press valve body 50 against valve seat 52 to shut off relief valve 26. Accordingly, as cap 30 is threadedly rotated downwardly over riser 56, greater pressure is applied to the compressive spring 54 and correspondingly on relief valve body 50 thereby requiring a greater gas pressure in cavity 49 to open relief valve 26. Spring 54 is selected to correspond with the pressures at which internal gas pressure in cavity 49 will cause valve body 50 to be opened and permit the escape of gases through the relief valve 26. Rotation of cap 30 changes the compression of spring 54 and, therefore, the pressures required to raise valve body 50 from valve seat 52.

THE METHOD

The method of this invention includes connecting valve 10 to inflation lumen 20 either before or after the endotracheal tube 12 has been preselected according to size and inserted into the tracheal passage of a patient (not shown) according to conventional techniques.

Valve 10 is securely engaged with the inflation lumen 20 and the operating personnel (not shown) closes pressure relief valve 26 by rotating cap 30 until boss 58 contacts and presses valve body 50 against valve seat 52. With pressure relief valve 26 closed, the cuff 14 is inflated sufficiently to suitably seal the tracheal passage (not shown).

Spring 54 may be coordinated during manufacture to correspond with preselected pressure settings as indicated by indicia 60 in cooperation with marker 62. For example, indicia 60 may be selectively placed around the periphery of cap 30 and coordinated with the resulting changes in spring tension of spring 54 to provide pressure relief valve 26 with incremental pressure settings of 25 millimeters of mercury for each indicia change.

Suitable pressure setting indicia have been found to be between 25 and 200 millimeters of mercury with each indicia 60 indicating a change of 25 millimeters of mercury pressure. Clearly, other suitable pressure setting indicia may be used, however, the foregoing settings are presently preferred. The last indicia is incorporated to indicate a fully shut position, that is, with boss 58 firmly pressed against valve body 50 to prevent the raising of valve body 50 from valve seat 52.

The minimal pressure setting required to maintain this pressure with the cuff 14 is then determined by backing off cap 30 and, correspondingly, boss 58 until a desired balance is achieved between the compressive force of spring 54 and gas pressure in cuff 14. Spring 54 thereafter maintains valve body 50 in a closed position until gas pressure in cuff 14 increases sufficiently to force pressure relief valve 26 to open at which time gas escapes until the pressure again drops to the preselected setting.

During periods of extended use, diffusion of anesthetic gas through the membrane and into inflatable cuff 14 causes an increase in pressure in inflatable cuff 14. This increased pressure is transmitted into the pressure relief valve 26 and there released. Accordingly, the novel apparatus of this invention enables the operating personnel to quickly and properly inflate the inflatable cuff 14 to seal the tracheal passage and thereafter obtain a pressure relief setting for the pressure relief valve 26 which will automatically release excessive pressures in the inflatable cuff 14.

The materials of construction of the present invention, with possibly the exception of the springs, may be any suitable plastic material for ease of fabrication, sterilization and ready disposability, if desired.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A pressure relief valve for a cuff on an endotracheal tube having an inflatable cuff which is inflated with an inflation device probe, the pressure relief valve comprising in combination:

a valve body;

an inlet into the valve body, the inlet having a manually operable inlet valve comprising an inlet valve seat and a valve head held against the inlet valve seat by an inlet spring, the valve head having an axial stem extending through the inlet valve seat into the inlet for engagement and movement of the valve head away from the inlet valve seat when the inflation device probe is inserted into the inlet, the stem having a notch in its end to permit escape of gases from the inflation device probe when the same is an engagement with the stem, the inlet valve selectively obstructing the inlet into the valve body with an inlet spring resiliently urging the valve head to the closed position to maintain inflation pressure within the cuff;

an outlet from the valve body operable to communicate gases from the inlet to an inflation lumen of the cuff; and a pressure relief valve in the valve body, the pressure relief valve comprising a riser and a cap threadedly engageable on the riser, the riser including a relief valve seat and a valve body which is held against the relief valve seat by a relief spring, the relief spring cooperating between the valve body and the cap so that rotation of the cap adjusts the compression of the relief spring and, correspondingly, the pressure in the valve body at which the pressure relief valve will open, the valve head being adjustably spring biased to the closed position, the valve head and cap including indicia and the relief spring being coordinated with the indicia to provide predetermined incremental pressure settings, the pressure relief valve thereby being operable to release elevated pressures in the valve body above the adjusted pressure setting.

2. A pressure relief valve as defined in claim 1 wherein the pressure relief valve includes means for holding the pressure relief valve in a closed position, said means comprising a boss on the cap, downward rotation of the cap causing the boss to press the valve head against the relief valve seat.

3. A method for relieving elevated pressures in an inflatable cuff on an endotracheal tube, comprising the steps of:

obtaining a pressure relief valve comprising the steps of:

fabricating a valve body having at least three openings therein;

inserting a manually operable valve in a first opening of the valve body, the first opening thereby serving as an inlet to the valve body holding the inlet valve closed except while inflating the cuff;

preparing an adjustable, spring-biased pressure relief valve and inserting it in a second opening to the valve body; and providing the third opening with means for communicating gas pressures between the valve body and an inflatable cuff on an endotracheal tube;

connecting the pressure relief valve to an inflatable cuff on an endotracheal tube;

inflating the cuff; and maintaining a constant preselected pressure setting within the cuff by adjusting the pressure relief valve to a preselected setting to relieve pressures in the valve body and cuff above the preselected setting.

* * * * *